United States Patent
Ellman

(10) Patent No.: US 10,667,858 B2
(45) Date of Patent: Jun. 2, 2020

(54) DEPTH CONTROL FOR ELECTROSURGICAL ELECTRODE

(71) Applicant: Alan Ellman, Hewlett, NY (US)

(72) Inventor: Alan Ellman, Hewlett, NY (US)

(*) Notice: Subject to any disclaimer, the term of this patent is extended or adjusted under 35 U.S.C. 154(b) by 323 days.

(21) Appl. No.: 15/597,039

(22) Filed: May 16, 2017

(65) Prior Publication Data

US 2017/0333118 A1 Nov. 23, 2017

Related U.S. Application Data

(60) Provisional application No. 62/337,802, filed on May 17, 2016.

(51) Int. Cl.
*A61B 18/14* (2006.01)
*A61B 17/00* (2006.01)
*A61B 90/00* (2016.01)
*A61B 18/00* (2006.01)

(52) U.S. Cl.
CPC .......... *A61B 18/1482* (2013.01); *A61B 2017/00407* (2013.01); *A61B 2017/00429* (2013.01); *A61B 2018/00196* (2013.01); *A61B 2018/00339* (2013.01); *A61B 2018/00946* (2013.01); *A61B 2018/1475* (2013.01); *A61B 2090/034* (2016.02); *A61B 2090/062* (2016.02); *A61B 2090/0811* (2016.02)

(58) Field of Classification Search
CPC .......... A61B 5/15019; A61B 5/150198; A61B 2018/1475
See application file for complete search history.

(56) References Cited

U.S. PATENT DOCUMENTS

| | | | |
|---|---|---|---|
| 5,843,091 A * | 12/1998 | Holsinger | A61B 18/1492 606/108 |
| 6,352,533 B1 | 3/2002 | Ellman | |
| 7,101,370 B2 | 9/2006 | Garito | |
| 7,137,982 B2 | 11/2006 | Garito | |
| 7,905,882 B1 * | 3/2011 | Ellman | A61B 18/1477 600/106 |
| 8,409,194 B1 | 4/2013 | Ellman | |
| 2004/0077973 A1 * | 4/2004 | Groenke | A61B 10/025 600/567 |
| 2008/0167653 A1 * | 7/2008 | Watlington | A61B 17/1615 606/81 |
| 2010/0023006 A1 * | 1/2010 | Ellman | A61B 18/1482 606/45 |
| 2015/0201947 A1 * | 7/2015 | Hill | A61B 17/12031 606/157 |

* cited by examiner

*Primary Examiner* — Jaymi E Della

(57) ABSTRACT

One embodiment of the present invention relates to an electrosurgical handpiece that has a first main body and a second main body. A squeezable handle connects to and across the first main body and the second main body such that, when the handle is unsqueezed, the first main body and the second main body assume a first position relative to one another. When the handle is squeezed, the first main body and the second main body assumes a second position relative to one another. An active electrosurgical electrode is slidingly mounted within the second main body and extends from the second end. A spacer is positioned around and in sliding engagement with the smaller diameter region of the first main body.

2 Claims, 8 Drawing Sheets

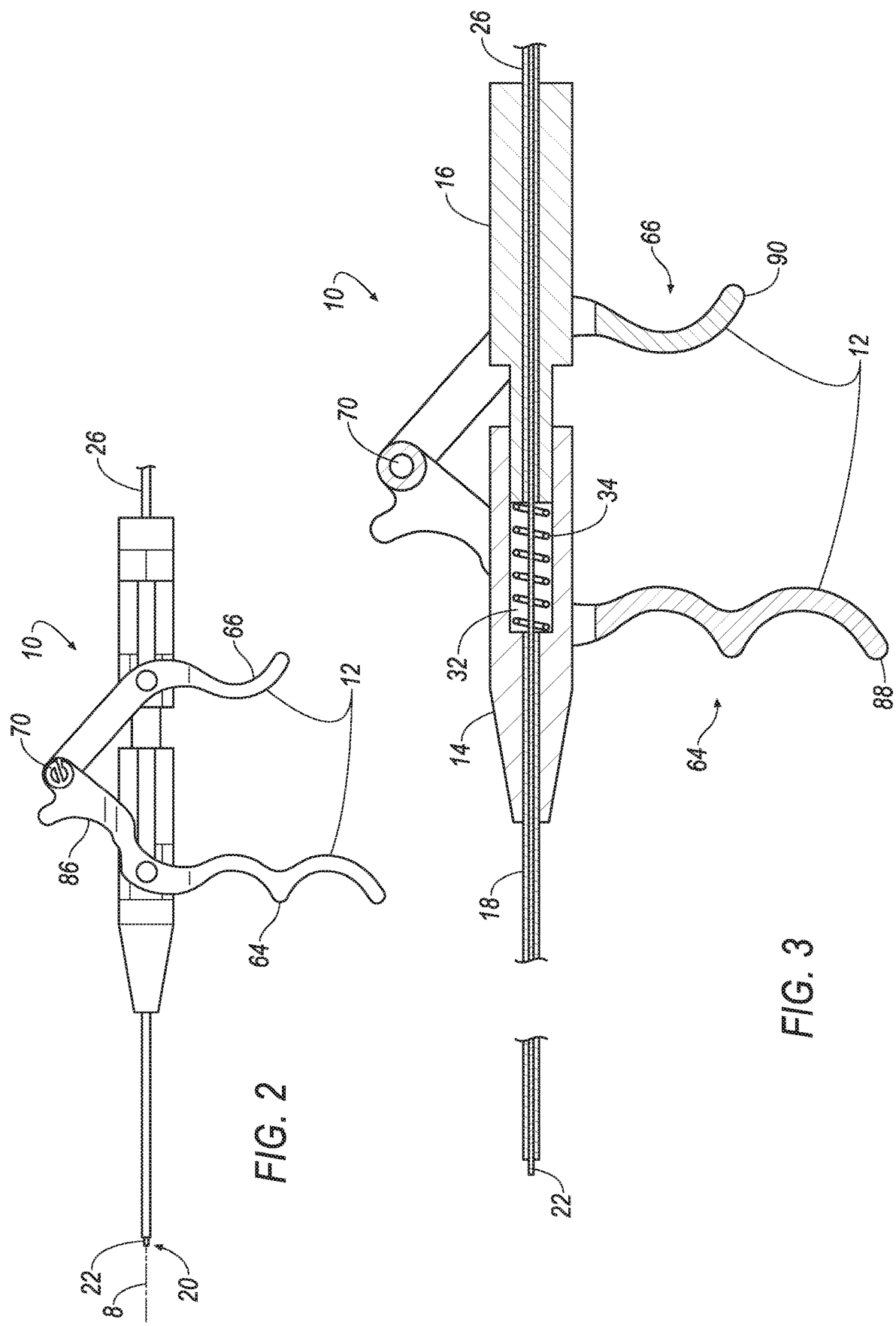

DEPTH CONTROL FOR ELECTROSURGICAL ELECTRODE

This Application claims priority to U.S. Provisional Patent Application No. 62/337,802 entitled Depth Control for Electrosurgical Electrode, filed May 17, 2016, the entirety of which is hereby incorporated by reference.

BACKGROUND

The present invention relates to surgery and, more specifically, the present invention relates to back surgery. Specialized back surgery on or in-between vertebrae of the spine and on spinal discs involves various meticulous surgical procedures which can be challenging, even for experienced surgeons who specialize in this particular surgery. Minimally invasive techniques are preferred over traditional open surgical procedures which require extensive operating time and post-operative recovery time.

When employing minimally invasive surgical techniques on or between spinal vertebrae or on discs, one of the challenging requirements relates to providing electrodes of an electrosurgical device into the operative field. More specifically, care must be taken to ensure that the electrode penetrates the vertebrae or other areas of the spine to a proper depth. To accomplish this, surgeons often are careful when positioning or actuating electrosurgical instruments to ensure that electrode only travels a certain distance into the operative field.

SUMMARY OF THE INVENTION

One embodiment of the present invention relates to an electrosurgical handpiece that has a first main body having a larger diameter region and a smaller diameter region. The larger diameter region has a first main body face extending radially from the smaller diameter region to the larger diameter region.

a second main body has an outer surface and an axially oriented aperture defining an inner surface. The second main body has a second main body face axially extending from the inner surface to the outer surface, wherein the inner surface slidingly engages the smaller diameter region of the first main body. The first main body face faces the second main body face. The second main body has a first end proximate the first main body and a second end distally located from the second main body.

A squeezable handle connects to and across the first main body and the second main body such that, when the handle is unsqueezed, the first main body and the second main body assume a first position relative to one another. When the handle is squeezed, the first main body and the second main body assumes a second position relative to one another.

A spring is located in the aperture and biases against the smaller diameter region to bias the first main body and the second main body into their first position.

An active electrosurgical electrode is slidingly mounted within the second main body and extends from the second end. The active electrosurgical electrode is affixed to the first main body.

A spacer is positioned around and in sliding engagement with the smaller diameter region of the first main body. The spacer has a first face facing the first main body face and a second face facing the second main body face.

The first face contacts the first main body face and the second face contacts the second main body face when the first main body and the second main body are in the second position.

An axial width of the spacer controls a length at which the active electrosurgical electrode extends from the second end of the second main body.

BRIEF DESCRIPTION OF THE DRAWINGS

FIG. 2 is a plan view of an electrosurgical instrument according to one aspect of the invention;

FIG. 3 is a cross-sectional view of an electrosurgical instrument according to an aspect of the invention;

DETAILED DESCRIPTION OF PREFERRED EMBODIMENTS

Figure 1:
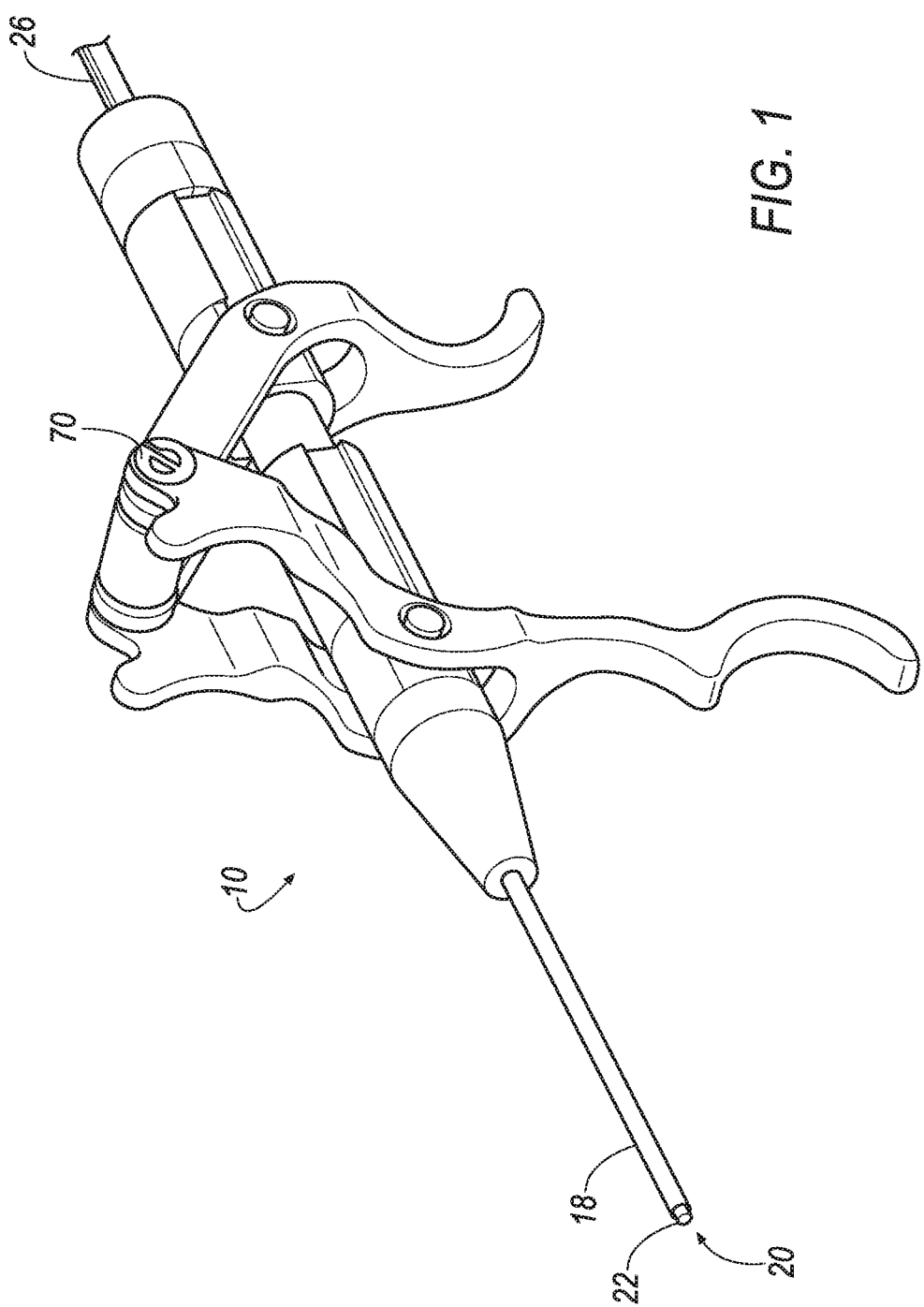
FIG. 1 is a perspective view of an electrosurgical instrument according to one aspect of the invention.
Figure 4:
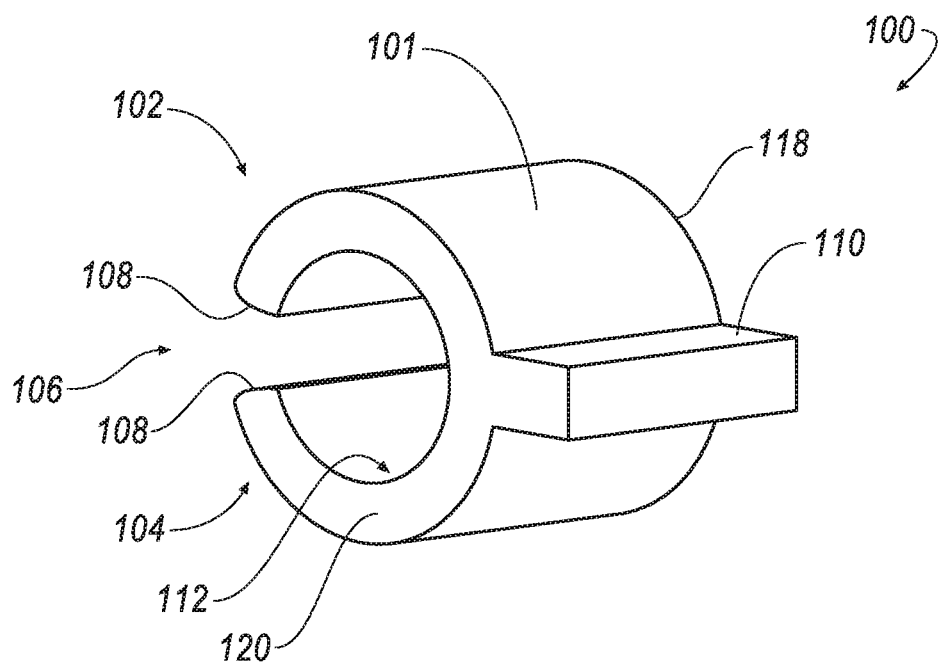
FIG. 4 is a perspective view of a spacer according to an aspect of the invention.

FIGS. 1 and 2 show one form of electrosurgical handpiece 10 according to one aspect of the invention, FIG. 3 shows a cross-sectional view, and FIG. 4 shows another form of electrosurgical handpiece 10. The present application incorporates U.S. Pat. Nos. 7,101,370; 6,357,533 and 7,905,882 in their entirety by reference. It will be observed that the cross-sectional view of the handpiece interior of FIG. 3 is identical to that of FIG. 2. It comprises a squeezable handle 12 assembly connected to and across two front 14 and rear 16 main slideable coaxially-aligned body parts enclosing an elongated outer tubular housing 18 from whose distal end 20 an inner electrode assembly 22 can be extended and retracted when the handle 12 is squeezed or released, respectively. The handpiece common axis is designated 8 in FIG. 2. At the right end an electrical cord 26 is terminated in a plug connector (not shown). Internally of the handpiece, wires of the electrical cord 26 are connected to the active electrode assembly 22. The outer tubular housing 18 extends from the front at the left and through the center of the front body part 14. Although the tubular housing 18 is shown as tubular or cylindrical, it will be appreciated that other shapes such as diamond, oval, square or any other shape may be employed. The front body part 14 contains a bore 32 which houses a compression spring 34 engaged by a reduced diameter projecting member of the rear body part 16. The compression spring 34 biases apart the two body parts 14, 16. In one aspect, the handle 12 keeps the body parts 14, 16 from relatively axially rotating. However, the body parts may be keyed or other means to keep the two body parts from rotating. Each of the front and rear handle parts, designated generally 64 and 66, are rigid members from their lowest points, designated 88, 90, to where they join at the fulcrum axis 70. The electrode assembly, in one aspect, is affixed in rear body part 16 and slidable in tubular housing 18 such that squeezing of handle 12 causes electrode assembly 22 to extend from distal end 20.

Referring now to FIG. 4, a spacer according to one aspect of the present invention is shown and described. Generally, the spacer is used in connection with an electrosurgical instrument to control the depth at which the electrode, extending from the instrument, penetrates the operative field during surgery. In the illustration, the spacer 100 is generally cylindrical in shape having an outer surface 101 and an inside diameter or ID 112. An entrance 106 is shown that provides a passage from the external environment around the spacer 100 into the interior for reasons that will be described. Chamfer regions 108 are located at the entrance 106 on each of the upper portion 102 and lower portion 104. A tab or grip 110 extends from the outer surface 101. In one aspect the grip 110 has gnarling or abrasive surfacing to permit easier gripping by an individual using the spacer.

Figure 6A:
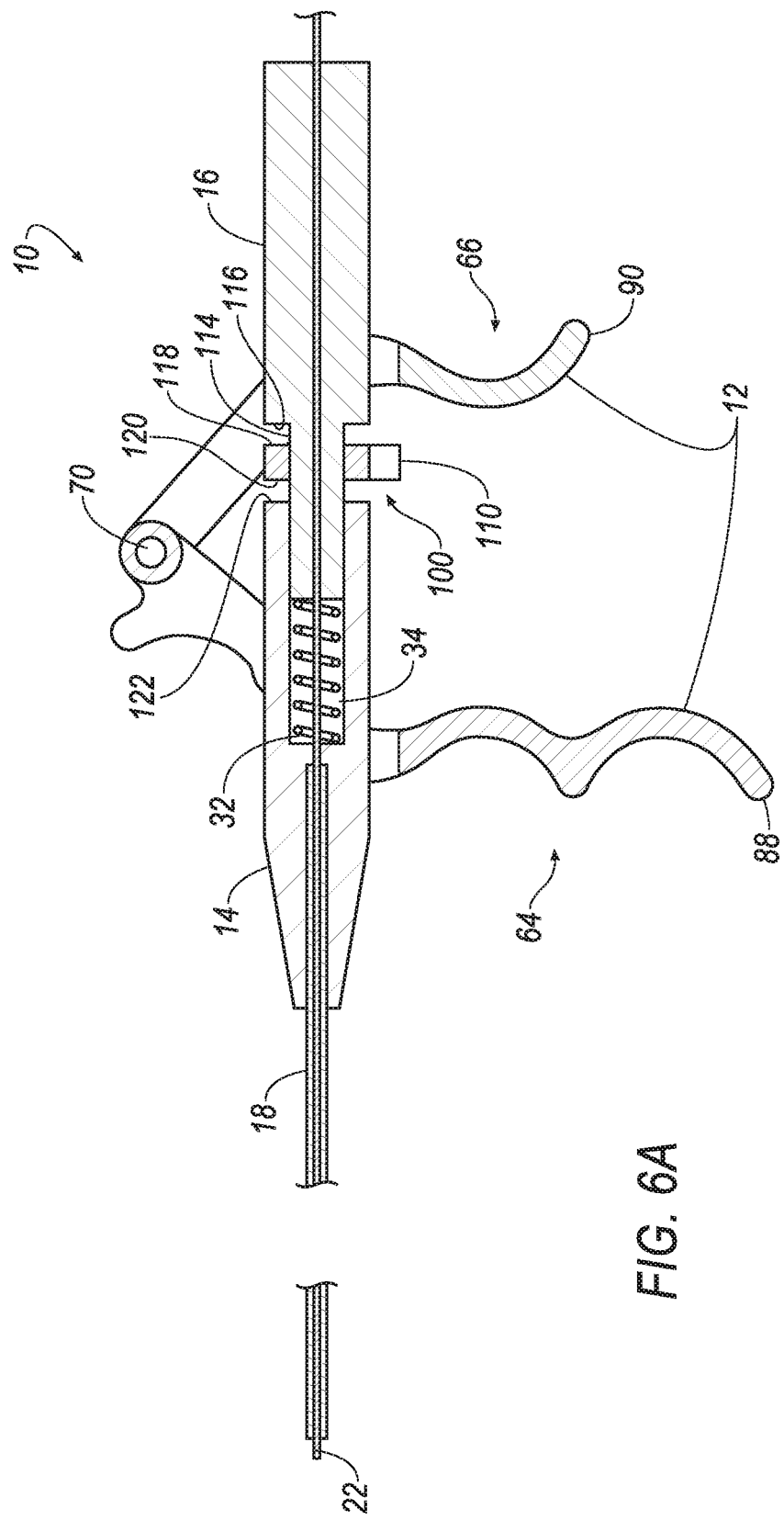
FIG. 6A is a cross sectional view of an electrosurgical instrument with a spacer according to an aspect of the invention.
Figure 6B:
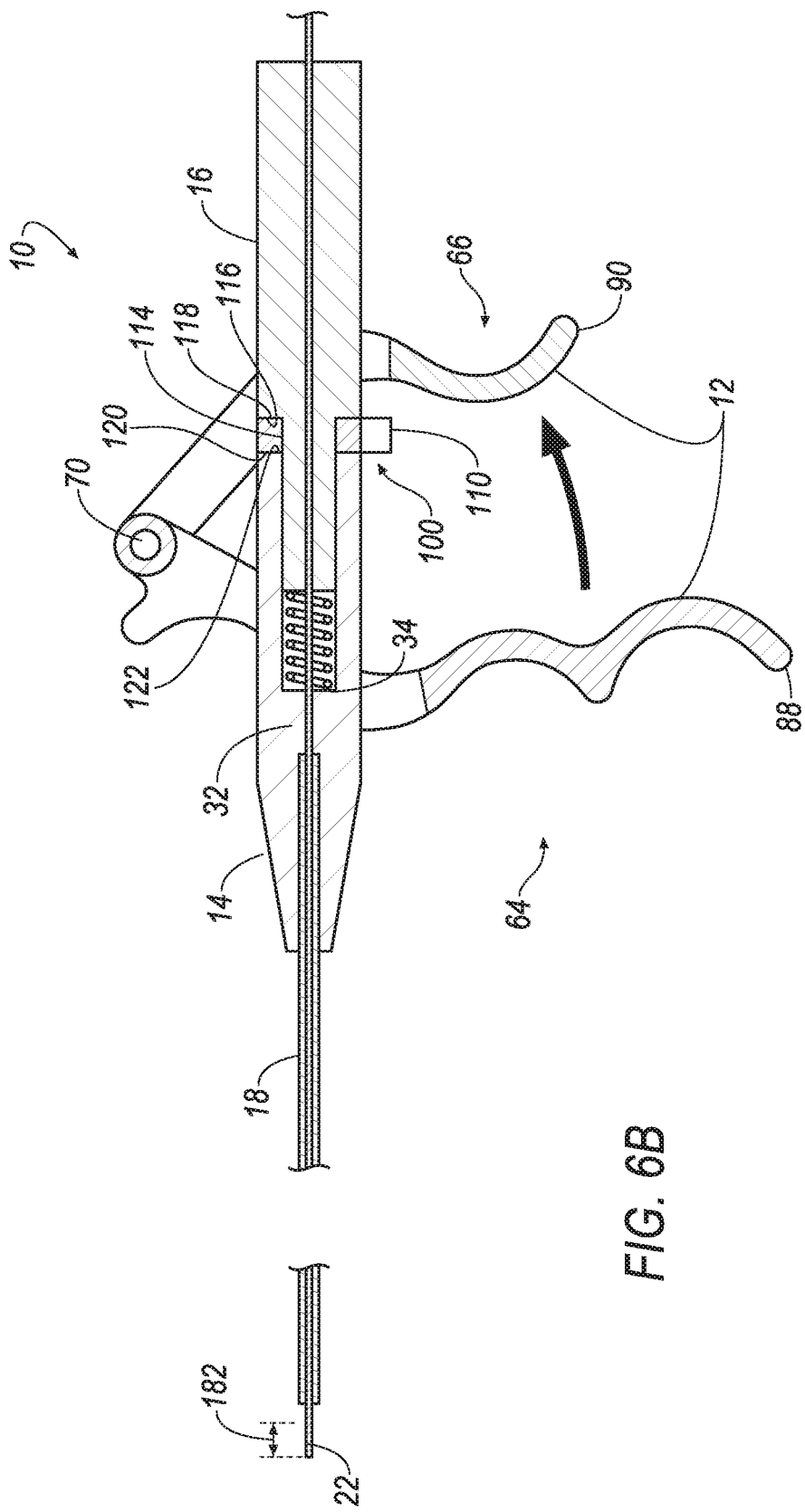
FIG. 6B is a cross sectional view of an electrosurgical instrument with a spacer according to an aspect of the invention.

Referring to FIG. 6A, spacer 100 is shown being used in conjunction with an electrosurgical instrument 10. In the illustration, spacer 10 encapsulates outside diameter or OD 114 of the body part 16 that engages with the body part 14. As such, in one embodiment, ID 112 rides atop OD 114 such that ID 112 and OD 114 are in sliding engagement. Accordingly, in operation, when the handles 12 are actuated, as shown in FIG. 6B, face 116 approaches face 118. Likewise, face 120 approaches face 122 until each of the respective faces contact each other. Once these faces contact, the movement of the body part 16 stops with respect to body part 14 and the travel of the electrode 22 exiting the electrosurgical instrument is set. Accordingly, the width of the spacer 110 dictates the amount of travel that body part 16 can travel with respect to body part 14. Thus, for example, looking at FIG. 6B, the distance the electrode is able to extend from the end of the electrosurgical instrument is shortened by distance 182 which corresponds to the width of the spacer.

To position the spacer 110 around OD 114, grip 110 is first gripped by the fingers of the surgeon or the operator. Next, the surgeon presses the chamfer regions 108 against the OD 114 such that the elastic material of the spacer 100 flexes to permit upper portion 102 to move away from lower portion 104 and permit the upper portion 102 and lower portion 104 to slide over the OD 114. The spacer may be made of a malleable or flexible material, soft plastic or rubber, to permit elastic deformation of the spacer to move around the OD 114.

Figure 5:
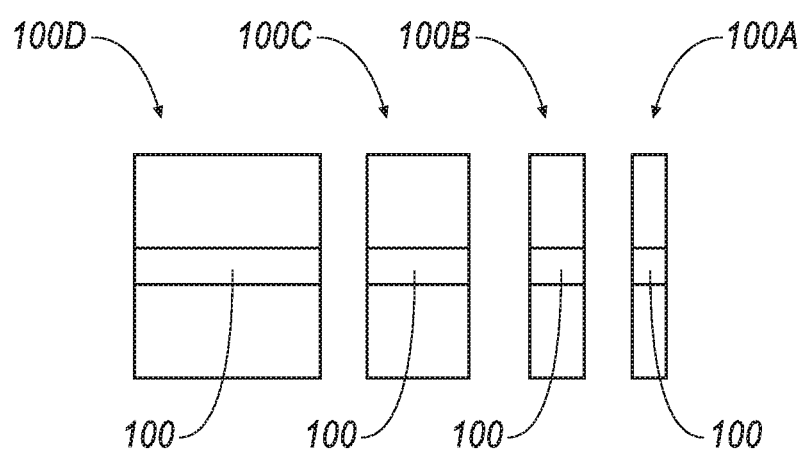
FIG. 5 is a plan view of a set of spacers according to an aspect of the invention.

As shown in FIG. 5, spacer 100 may come in a set of multiple spacers 100A, 100B, 100C, and 100D. Each of the spacers has a different width to provide depth control of an electrosurgical instrument to a different depth. For example, in one embodiment, the surgeon may select spacer 100A which has a relatively thinner thickness to provide a relatively deeper depth or may select spacer 100D that has a relatively thicker thickness to obtain a relatively shallower depth.

Figure 7:
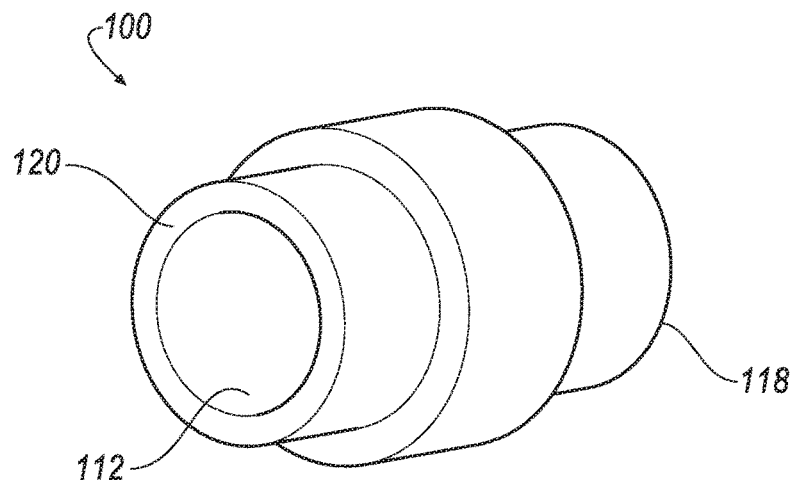
FIG. 7 is a perspective view of a spacer according to an aspect of the invention.

Referring now to FIG. 7, another embodiment of the present invention is shown and described. In FIG. 7, a perspective view of the spacer 100 according to another aspect is illustrated. In the embodiment of FIG. 7, spacer 100 is shown as a fully encapsulated cylinder without any entrance such as entrance 106 in FIG. 4. As such, spacer 100 of FIG. 7 is intended to reside permanently on the electrosurgical instrument at the location where spacer 100 is shown in FIGS. 6A and 6B. In the present embodiment, adjustment, as will be described, of the spacer 100 changes the overall width of the spacer to change the resulting depth at which the electrode of the electrosurgical instrument may penetrate the operative field.

Figure 8:
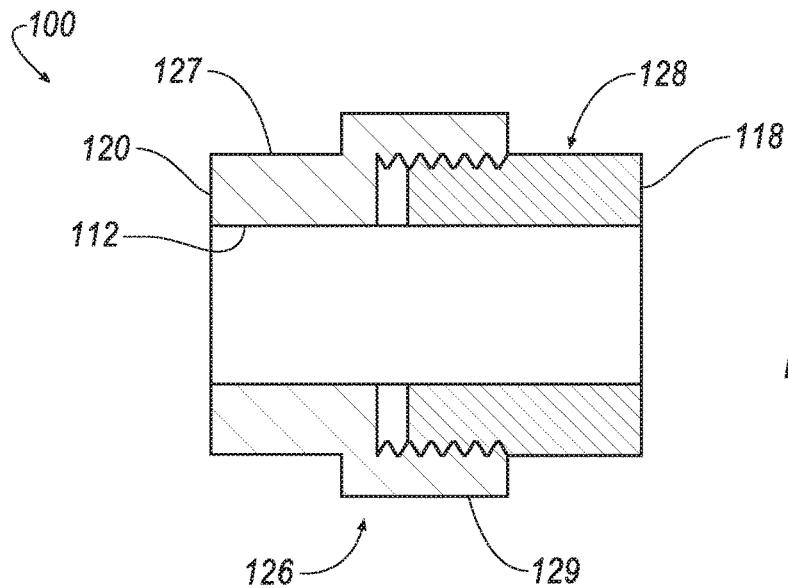
FIG. 8 is a cross sectional view of a spacer according to an aspect of the invention.

With reference to FIG. 8, a cross-section of the spacer 100 is shown. In FIG. 8, spacer 100 is shown having a first portion 126 and a second portion 128. The first portion 126 has a smaller outside diameter area 127 and a larger outside diameter area 129. The second portion 128 includes threads located at an outside diameter of a portion residing next to and under the larger outside diameter area 129 of the first portion 126. The threads on the outside diameter of the second portion 128 engage threads on the inside diameter of the larger outside diameter portion 129. As such, the first portion 126 may be threaded together with the second portion 128.

The first portion 126 may be threaded toward or away from second portion 128. In response thereto, the distance between face 118 and face 120 expands and contracts depending on which direction the two bodies are rotated with respect to one another. This movement changes the width of the overall spacer 110 to adjust the resulting depth of the electrode on the electrosurgical instrument similar to different choices of spacer with in the embodiment described with respect to FIG. 4. Thus, the overall distance 182 is a function of the width of the spacer which is changed as a function of the rotation of portions 126 and 128.

Figure 9:
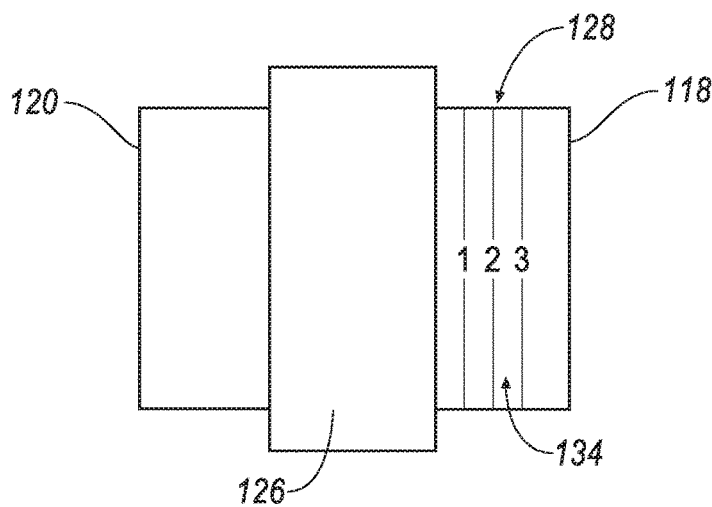
FIG. 9 is a plan view of a spacer according to an aspect of the invention.

With reference to FIG. 9, the outer surface of second portion 128 is shown including markings 134. The markings 134 may include various depth information (shown in this embodiment as 1, 2, and 3) that illustrates the depth or with of the spacer 100 or the penetration of the electrode into the operative field or any other meaningful information relating to the width of the spacer. One skilled in the art will understand that such depth or with may represent, for example, the depth at which the electrode of the electrosurgical instrument will penetrate the operative field or into a vertebrae for other spinal region. For example, instead of the number "1", a number such as 2 mm may be etched on the surface to indicate that such is the depth associated with a spacer 100 with first portion 126 and second portion 128 rotated to a particular position. Other markings might indicate into which area of the spine the electrode will extend. For example, a setting of 1 might result in penetration just into the annulus or other region which settings of 2 or 3 might result in different depths.

Figure 10:
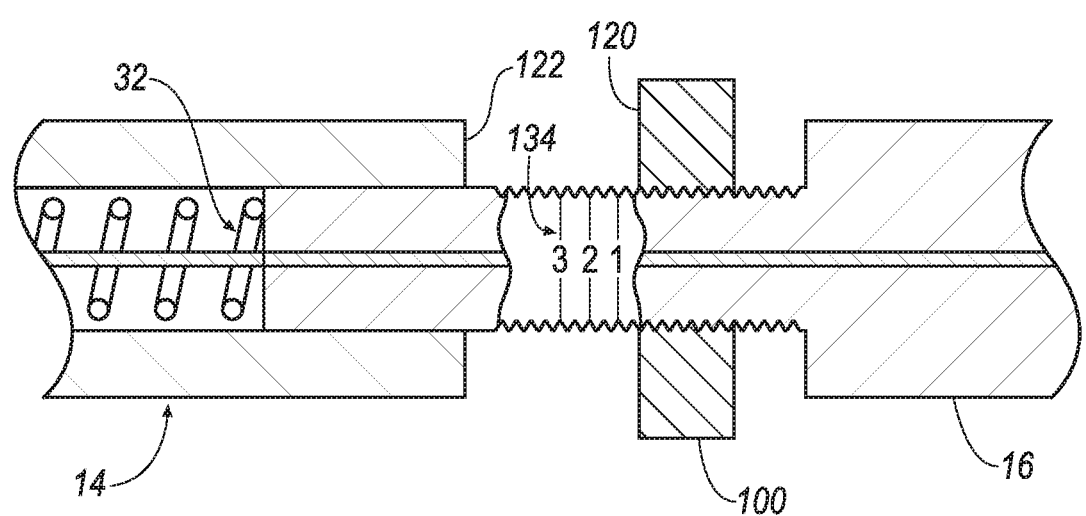
FIG. 10 is a plan view of a portion of an electrosurgical instrument according to an aspect of the invention.

Referring now to FIG. 10, another embodiment of the present invention is shown and described. In FIG. 10, the body part 16 is shown engaged to body part 14. Spacer 100 is shown having threads on its inside diameter that meet with threads on the outside diameter of the body part 16. Accordingly, spacer 100 may be rotated on threads around body part 16 to move the spacer 100 closer or away from body part 14. As such, face 120 gets closer or further from face 122, thereby setting a gap and resulting in a setting of the depth at which the electrode of the electrosurgical instrument may penetrate the operative field. Similar to the previous embodiment, markings 134 may be etched on the side of the body part 16 to permit a depth setting to be understood and set by the surgeon using the electrosurgical instrument.

Figure 11:
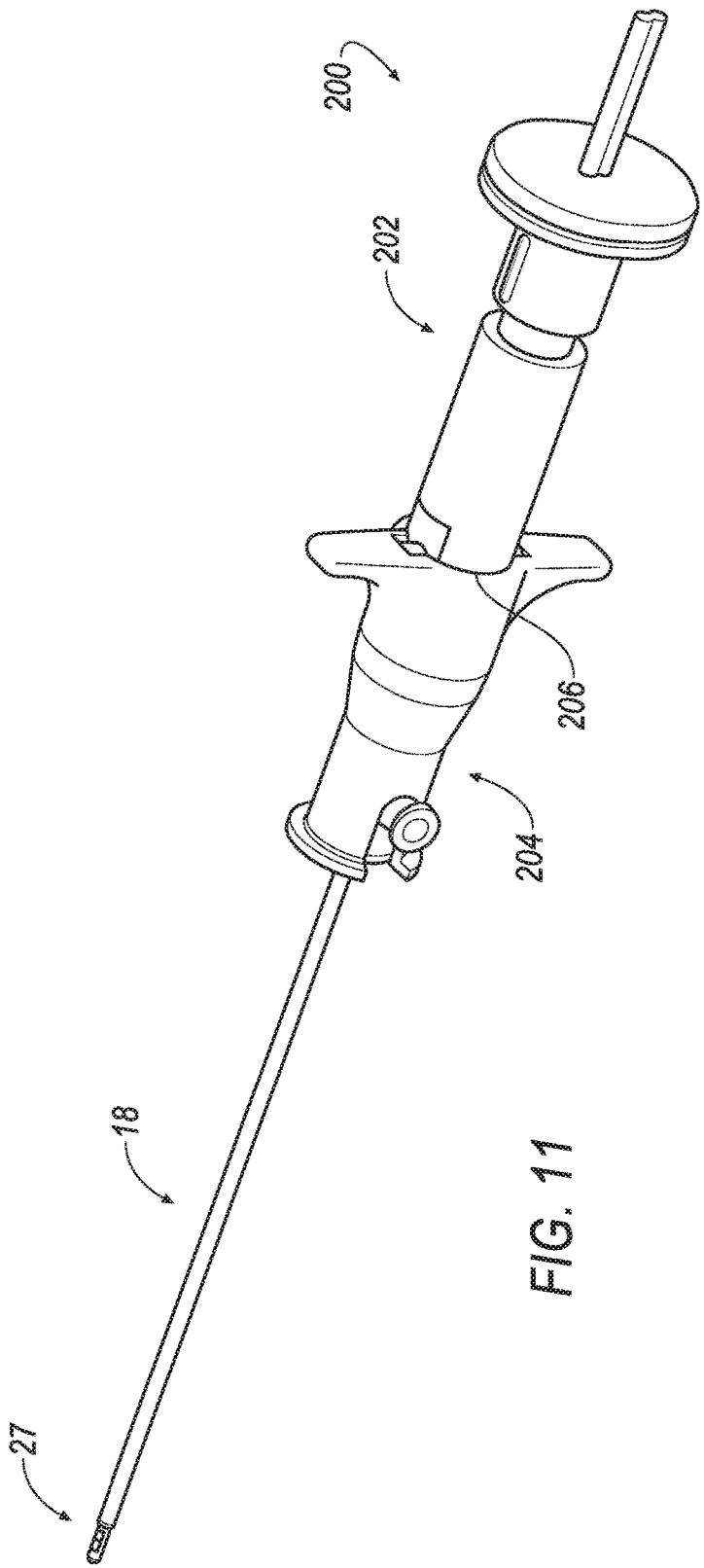
FIG. 11 is a plan view of a portion of an electrosurgical instrument according to an aspect of the invention.

Referring now to FIG. 11, another embodiment of the present invention is shown and described. In FIG. 11, an electrosurgical instrument 200 is shown having a plunger 202 slidingly engaged to a main body 204 through insertion of the plunger 202 into the main body 204 through the entrance 206. An electrode is fixedly connected to the plunger 202 and passes through the main body 204 such that it passes through the outer tubular housing 18. As seen in the figure, inner electrode assembly 22 extends from the outer tubular assembly 18. In operation, compression of plunger 202 into main body 204 causes the inner electrode assembly 22 to extend from the outer tubular housing similar to that described in previous embodiments.

Figure 12:
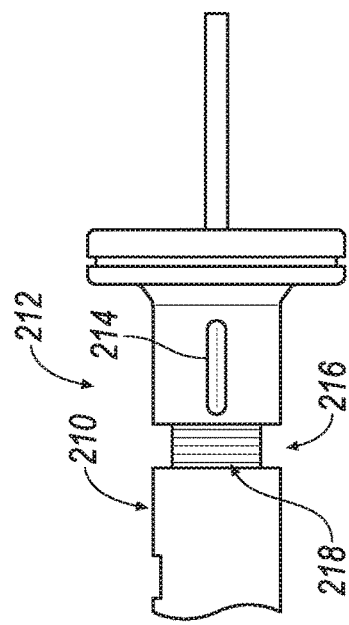
FIG. 12 is a plan view of a portion of an electrosurgical instrument according to an aspect of the invention.

Referring to FIG. 12, the plunger 202 is shown including a plunger portion 210 connected to a cap 212 by an inside region 216. Threads 218 circumscribe the outside surface of the inside region 216. While inside region 216 is affixed to plunger portion 210, cap 212 is threaded on threads 218 to allow cap to rotate closer to and farther from plunger portion 210. In one embodiment, raised portion 214 releases cap 212 upon pressing raised portion 214 to allow cap 212 to rotate about the threads to screw the cap down and up along the threads. When raised portion 214 is impressed, cap 212 can no longer rotate about the threads. By this way, rotation of the cap 212 can be actuated to control the depth of the electrode as discussed in previous embodiments and then locked into place once the desired depth is achieved.

Figure 13:
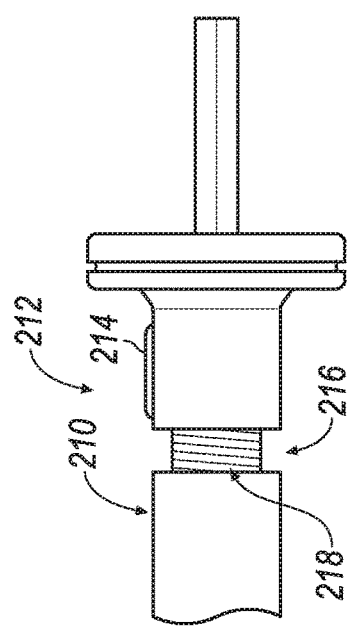
FIG. 13 is a plan view of a portion of an electrosurgical instrument according to an aspect of the invention.

Referring now to FIG. 13, another embodiment of the invention is described. In FIG. 13, threads 218 are formed as a set of ribs. Raised portion 214 rides along the top of the ribs to permit cap 212 to ratchet-like move toward and away from the plunger portion and set the depth. In this way, the cap portion 212 to be ratcheted in and out to set the desired depth.

In this specification, various preferred embodiments may have been described with reference to the accompanying drawings. It will, however, be evident that various modifications and changes may be made thereto, and additional embodiments may be implemented, without departing from the broader scope of the invention as set forth in the claims that follow. The present invention is thus not to be interpreted as being limited to particular embodiments and the specification and drawings are to be regarded in an illustrative rather than restrictive sense.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. An electrosurgical instrument comprising:
a first main body having a larger diameter region and a smaller diameter region, wherein the larger diameter region has a first main body face extending radially from the smaller diameter region to the larger diameter region;
a second main body having an outer surface and an axially oriented aperture defining an inner surface, the second main body having a second main body face radially extending from the inner surface to the outer surface, wherein the inner surface slidingly engages the smaller diameter region of the first main body, the first main body face facing the second main body face, the second main body having a first end proximate the first main body and a second end distally located from the second main body;
a squeezable handle connected to and across the first main body and the second main body such that, when the handle is unsqueezed, the first main body and the second main body assume a first position relative to one another, and when the handle is squeezed, the first main body and the second main body assumes a second position relative to one another;
a spring located in the aperture and biased against the smaller diameter region to bias the first main body and the second main body into their first position;
an active electrosurgical electrode slidingly mounted within the second main body and extending from the second end, the active electrosurgical electrode affixed to the first main body; and
a spacer positioned around and in engagement with the smaller diameter region of the first main body, the spacer having a first face facing the first main body face and a second face facing the second main body face;
wherein the first face contacts the first main body face and the second face contacts the second main body face when the first main body and the second main body are in the second position;
wherein an axial width of the spacer controls a length at which the active electrosurgical electrode extends from the second end of the second main body;
wherein the spacer completely encapsulates a circumference of the smaller diameter region of the first main body such that the spacer is non-removable from the smaller diameter region of the first main body;
wherein the spacer is slidingly attached to the first main body or the second main body;
the spacer further comprises a first spacer portion threadingly engaged with a second spacer portion such that rotation in one rotational direction expands the axial width of the spacer while rotation in an opposite rotational direction contracts the axial width of the spacer;

wherein the spacer slides freely along the smaller diameter region of the first main body when the when the handle is unsqueezed.

2. The electrosurgical instrument as claimed in claim 1, further comprising:

first main body threads positioned along an axial length of the smaller diameter of the first main body portion;

spacer threads positioned on an inside diameter of the spacer that are engaged with the threads of the first main body threads;

wherein rotation of the spacer moves the spacer with respect to the smaller diameter of the first main body portion to the length that the electrosurgical electrode extends.

\* \* \* \* \*